(12) United States Patent
Taylor

(10) Patent No.: US 6,845,653 B2
(45) Date of Patent: Jan. 25, 2005

(54) COATING STRETCH TESTER

(76) Inventor: John A. Taylor, 12 Park Ave., Pompton Plains, NJ (US) 07444

( * ) Notice: Subject to any disclaimer, the term of this patent is extended or adjusted under 35 U.S.C. 154(b) by 0 days.

(21) Appl. No.: 10/748,605

(22) Filed: Dec. 30, 2003

(65) Prior Publication Data

US 2004/0149018 A1 Aug. 5, 2004

Related U.S. Application Data

(62) Division of application No. 10/131,966, filed on Apr. 25, 2002, now Pat. No. 6,701,778.

(51) Int. Cl.[7] ........................ G01N 11/06; G01N 13/02; G01P 15/00; G01B 121/02
(52) U.S. Cl. ................... 73/54.22; 73/53.13; 73/53.01; 73/64.48; 73/150 R; 73/488; 73/521; 73/861
(58) Field of Search .......................... 73/53.01, 54.13, 73/54.22, 64.48, 64.49, 64.51, 150 R, 488, 521, 861

(56) References Cited

U.S. PATENT DOCUMENTS 4,409,844 A * 10/1983 Schweiso ..................... 73/861

FOREIGN PATENT DOCUMENTS

DE 3011571 3/1980 ................ 73/64.51

* cited by examiner

Primary Examiner—Daniel S. Larkin
(74) Attorney, Agent, or Firm—Notaro & Michalos P.C.

(57) ABSTRACT

A test apparatus and method for predicting the minimum runnable flow of a curtain coating fluid by forcing the coating fluid out of a small round tube opening with less flow rate than is required for momentum to exceed the contracting forces of surface tension. The minimum flow rate is a measure of the combined effects of the surface tension, viscosity, elasticity, and dilitant behavior of the coating fluid which influence the stretch and acceleration of the fluid, that in turn, characterize the runnability of the fluid for a full scale curtain coating process. The velocity of the coating as it lands can also be determined from the flow rate and acceleration to predict whether the coating fluid will run or not before it is applied to a web or substrate.

21 Claims, 7 Drawing Sheets

U S 6,845,653 B2

COATING STRETCH TESTER

CROSS-REFERENCE TO RELATED APPLICATION

This is a divisional of application Ser. No. 10/131,966 filed Apr. 25, 2002 and now U.S. Pat. No. 6,701,778.

FIELD AND BACKGROUND OF THE INVENTION

The present invention relates generally to the field of curtain coating, and in particular to a new and useful apparatus and method for measuring the runnability of a coating process.

Curtain coating machines are used to create uniform coatings on a particular substrate. Prior techniques for curtain coating generally experience a large loss of coating material as a result of undue experimentation while attempting to achieve uniformity in the coating material. In particular, prior techniques for curtain coating have been unable to focus on the crucial fluid properties which dictate runnability and have instead used time-consuming and expensive trial and error techniques.

It is common for new coating formulas to be modified and operating conditions adjusted to achieve good appearance or uniform coating lay at full commercial conditions. This is done by trial and error with expensive commercial and pilot machine trials. It is expected that measurements taken according to the present invention will eliminate that practice as the important properties of the coating can be measured and adjusted prior to a run. It is common for formulas to be modified over the span of several months. Several (e.g., 8 to 10) runs are performed under programs costing $80,000 to $100,000. It is expected according to the invention that this expense will be avoided by measuring important properties of the coating material using beaker quantities of the material in the lab. With the coating formula properly adjusted the trial effort will be considerably reduced and good results achieved on the first run.

Development of a suitable curtain coating is important, with many companies spending large sums of money to formulate such coating material. The material must lay down in a perfectly uniform coating thickness, and this is possible with curtain coating. Perfect uniformity has made curtain coating the coating technique of choice for photographic and other imaging paper applications, because the layer of coating is developed to a solid color and any non-uniformity can be seen easily. This coating method has high process efficiencies with little operating adjustments required. The uniformity advantages combined with improved efficiency make it very interesting for a broad range for coated products.

Various methods are known for measuring fluid properties. U.S. Pat. No. 5,590,560, for example, teaches an apparatus and method for measuring dynamic viscosity, surface tension and dilational elasticity. Electrostatic forces are used to distort a film rather than gravity and an air jet as with the present invention. The apparatus of U.S. Pat. No. 5,590,560 is measuring surface dilatational elasticity and not the bulk properties of dilitation index and bulk elasticity. The time for full distortion is 0.1 seconds as taught by the patent. The invention achieves distortion in 0.8 milliseconds. The prior patented apparatus is measuring the surface distortion force under compression whereas the invention is measuring under stretching. The prior apparatus is not measuring the same thing as the invention.

U.S. Pat. No. 5,590,560 teaches distorting a film of coating to twice its thickness. So, if one thinks of the motion of something flat and uniform being pulled up into a sine wave it is the opposite to what the invention is testing. The fluid is bunching up, not thinning out. The volume/diameter is getting smaller whereas in the inventive test the volume/diameter is getting larger.

U.S. Pat. No. 5,792,941 discloses a method for determining dynamic physical properties such as surface tension and viscosity. A base is provided with an open channel having a predetermined cross-section and height, and a fixed distance is identified within the channel. The liquid to be tested is deposited in the channel and a measurement is taken of the time that the liquid requires to flow through the fixed distance.

U.S. Pat. No. 6,185,989, for example, teaches a device for dynamic measurement of the surface tension of a liquid by a bubble pressure process. Gas pressure is used to form a boundary between liquid and gaseous surface, and an electrically operated device may then measure the pressure inside the bubble.

One curtain coating method has been developed for measuring static and dynamic surface tension, but has failed to address other fluid properties of a coating that are relevant for measuring and improving runnability of a coating. U.S. Pat. No. 5,304,402 claims a curtain coating method in which a solution injector, having at each of two side ends an edge guide, applies a coating at a flow rate of 2 cc/(cm*sec). This prior method is able to achieve flow rates as low as 2 cc/(cm*sec) by restricting the horizontal movement of a coating solution in the freely falling coating film by adjusting the width and the radius of the solution contacting surface of the edge guide based on the measurements of static and dynamic surface tension.

The following articles and patents disclose various curtain coating techniques and characteristics:

1. D. R. Brown, *A Study of the Behaviour of a Thin Sheet of Moving Fluid*, Journal of Fluid Mechanics, Vol. 10, part 2, pages 297–305;
2. W. Van Abbeyenyen, W. Mues, B. Goetmaeckers; Agfa-Gevaert in an unpublished presentation at an AIChE meeting circa 1990;
3. Summers et al., *The Kinematics and Dynamics of Free Surface Coating Fluids*, Final Report on *EPSRC* Grant GR/L17191, June 2000; and
4. U.S. Pat. Nos. 4,216,290; 5,824,887; and 5,962,075.

The following additional patents disclose fluid testing techniques: U.S. Pat. Nos. 4,196,615; 4,646,562; and 5,479,816.

Although several examples have been given of methods for determining fluid properties, relevant to the runnability of a coating, no known method addresses measurement of each of the fluid properties that are necessary for predicting the runnability of a coating for a curtain coating machine.

SUMMARY OF THE INVENTION

It is an object of the present invention to provide an apparatus and method for determining the runnability of a coating based on fluid property measurements of the coating. The term "runnability" is used here to mean the characteristics of a coating material that gives reasonably satisfactory results when used to coat a substrate during a curtain coating run.

It is also an object of the present invention to provide an apparatus and method for measuring a coating's resistance to stretch underfree fall conditions. The resistance to stretch by a fluid is caused by a combination of the fluid's surface tension, viscosity, elasticity, and dilatant behavior. The central property measured is a new property called "stretch," which is actually a combination of surface tension and viscosity. A stretch number is derived from the minimum flow rate of a falling stream that is forced out of a small round tube with more flow rate than is required for momentum to exceed contracting forces of surface tension. Actual surface tension is measured if the viscosity is less than one centipoise or otherwise negligible.

It is another object of the present invention to provide an apparatus and method for determining the landing velocity of a coating when it makes contact with a moving sheet of substrate. The landing velocity can be measured from a combination of the stretch, acceleration, and viscosity.

Undesirable elasticity and dilatant behavior impede a fluid from stretching out and can be detected by measuring the acceleration of a falling stream.

Therefore, another object of the present invention is to provide an apparatus and method for measuring acceleration of a coating as it is observed falling between two points assuming a uniform accelerating force. The assumed accelerating force is the force of gravity, minus surface tension, elasticity, dilatant behavior, and viscosity, expressed in ft/sec/sec. Dilatant behavior refers to particle interactions that retard fluid flow such as particles jamming against each other in the fluid. Coatings for printing paper, for example, contain two micron diameter pigment particles which can flock together into six to eight micron clusters.

Accordingly, an apparatus and method are provided for measuring various fluid properties such as surface tension, viscosity, elasticity, and dilatant behavior, to predict the performance of the coating to be applied with a curtain coater, for testing and/or improving the runnability of the coating.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
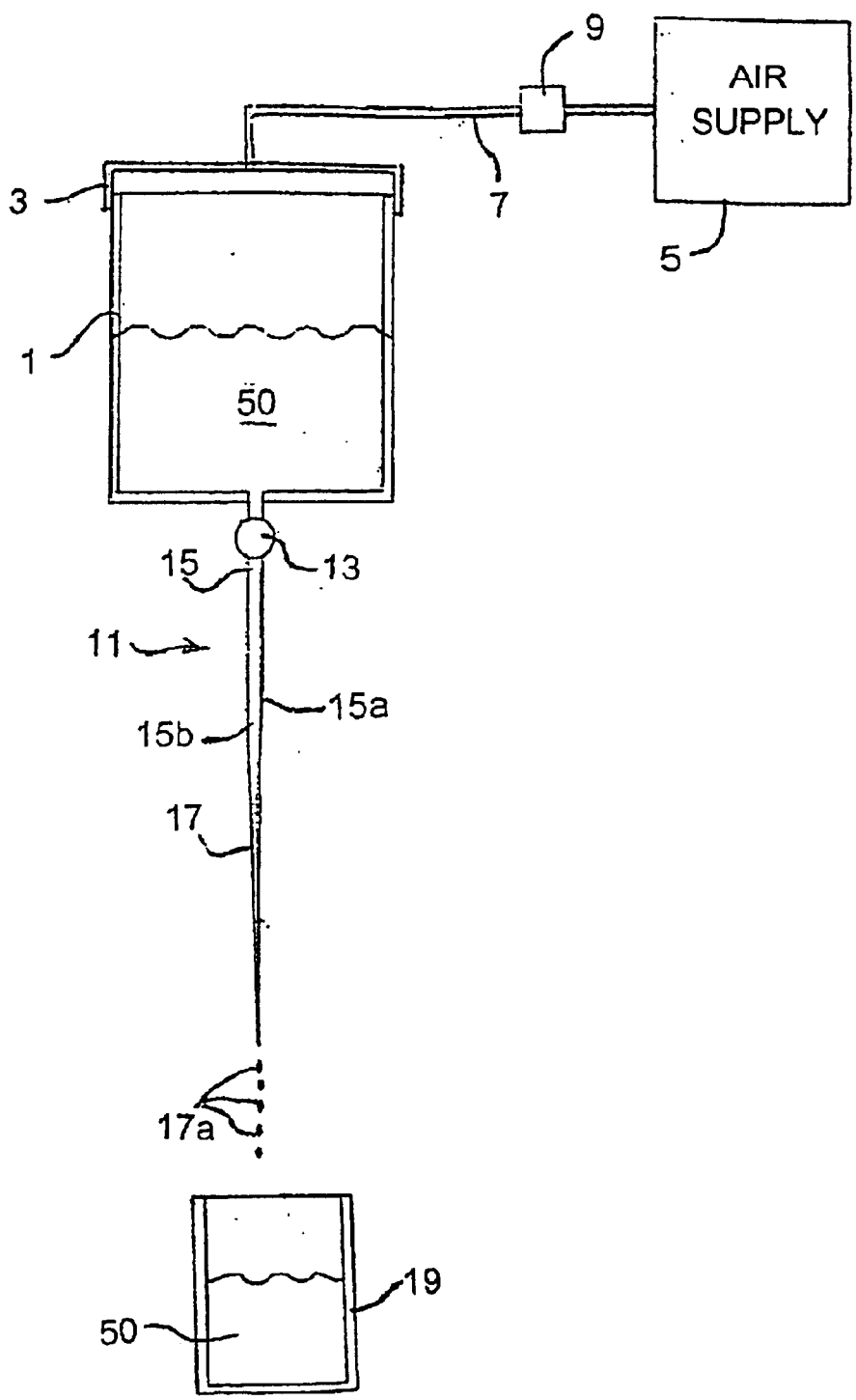
FIG. 1 is a schematic diagram of an apparatus of the invention for measuring stretch and acceleration of a coating material.

Referring now to the drawings, in which like reference numerals are used to refer to the same or functionally similar elements, FIG. 1 is a schematic diagram of a curtain coating test apparatus for determining the stretch and acceleration of a coating fluid or material. The apparatus accurately simulates certain critical characteristics of a curtain coating process, but using beaker sized quantities of the coating fluid only and no substrate. In this way, full sized curtain coating lines are not used, nor expensive substrates or large quantities of coating material.

In order to measure stretch and acceleration, a 1.0 liter pressure-adjustable container 1 is used for storing a quantity of a fluid material or coating 50. The container 1 has a removable lid 3, which can be locked. The container 1 is connected to an air supply 5 via an air tube 7. An air pressure valve 9 is used to reduce the pressure within the container 1. An outlet, generally designated 11, from the container has a needle valve 13 for coarse adjustment. Alternatively, the fluid may be pumped out of the container with a variable speed pump (not shown).

Outlet 11 includes a tube 15 with a tapered end 15a, a circular 0.020" diameter hole 15b, from which the fluid is released into a free fall state until it reaches an object below. The walls of the tube 15 are tapered at 15a so the open end 15b is a knife-edged annulus.

Though tubes are commercially available in various diameters, it has been found that commercially available tubes with a 0.020" diameter work best and they are preferred, although a range of 0.011" to 0.034" also works for the invention and for most commercial coatings. The preferred range is 0.015" to 0.030" for the tube diameter, however.

The inside diameter of the tube determines the operating range of the stretch measurement as well as the reproducibility of the test. Larger holes give more variable results, as do untapered tubes. The standard deviation increases by a factor of three, which is unacceptable. Smaller holes avoid the rapid contraction needed after the fluid exits the needle for this measurement of the invention to work, and smaller holes are much more difficult to keep clean and would require some kind of prefilter. According to the invention, a 0.010" tube is too small and a 0.035" tube is too large in most cases.

In the testing apparatus in FIG. 1, a stream of coating 17 is released to fall into a graduated cylinder 19 below; as part of the test for determining stretch and acceleration. The stream 17 contracts from the tube inside the diameter and forms drops 17a at the bottom. Each time a drop separates, the weight of the stream is reduced and the stream 17 jerks upward.

Figure 2:
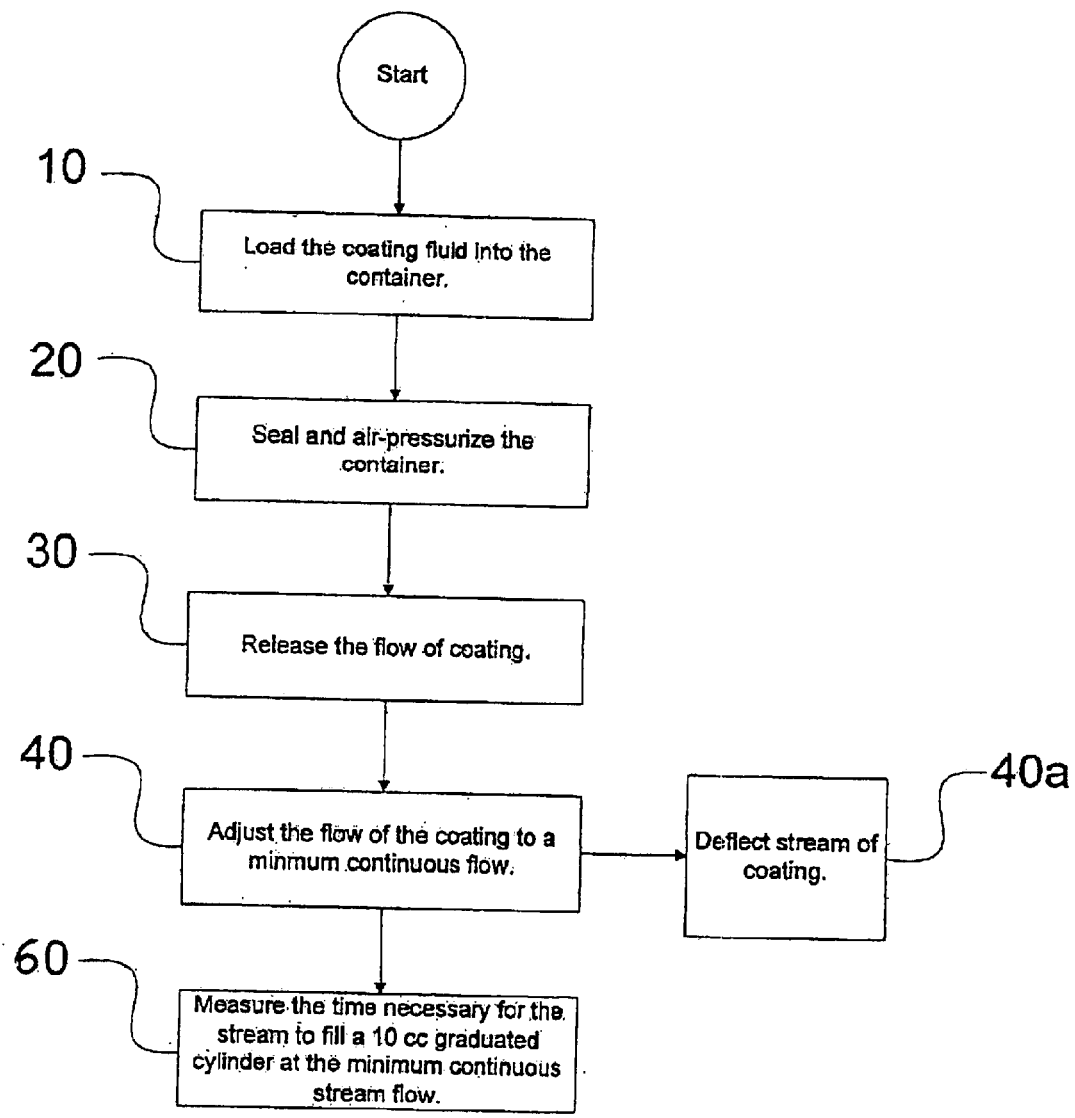
FIG. 2 is a flow chart of the method for determining stretch.

FIG. 2 is a flow chart fort he method of determining the minimum flow rate of a stream of coating according to the invention. In step 10, 100 cc of coating fluid is loaded into the testing container 1. The container 1 is then sealed by lid 3 and the air pressure is increased via the air pressure valve 9, in step 20. In step 30, the flow of coating is released by opening valve 13 and/or air pressure valve 9. In step 40, the flow rate of the sample coating fluid may be increased or decreased by coarse and fine adjustment of valve 13 and air pressure valve 9, until the coating fluid transforms from a series of drops 17a into a continuous, ripple-free stream 17, falling unbroken from the outlet opening 15b to the container 19 and which does not jerk up.

The stretch measurement is taken as the lowest flow rate needed to form a continuous ripple-free stream of the coating fluid 17, without jerk-up. In step 60, the lowest flow rate is measured by recording the time it takes to fill the 10 cc graduated cylinder 19 with the minimum continuous stream flow. Time can be measured by a stopwatch. The 10 cc graduated cylinder 19 is placed beneath the tube so that the coating fluid stream, free falls into it.

Alternatively, flow rate may also be measured by other suitable means known in the art such as a flow meter.

The continuous stream 17 of coating fluid should be as short as possible if it is stable. If the stream jerks upward, it should be 1" long. The incidence of the stream 17 jerking upward is satisfactory at surface tensions above 25–26 dynes/cm At surface tensions below 20 dynes/cm, there should be no jerking upward. Reformulation of the coating fluid is performed if the test is not achieved with the coating in the container. In this way coatings which would not run in a full scale curtain coating test are not used and the waste of unsuccessful full scale testing is avoided.

Elasticity and dilatantcy retard the acceleration of the stream 17 and prevents the stream from thinning. Therefore, the stream 17 should be carefully monitored so that there is continuous thinning, that is tapering from the opening 15b to the cylinder 19. The fluid may also flare out upon exiting from the outlet tube 15, but this is not fatal as there can still be good stretch. Excessive flare should be avoided, however.

Figure 5:
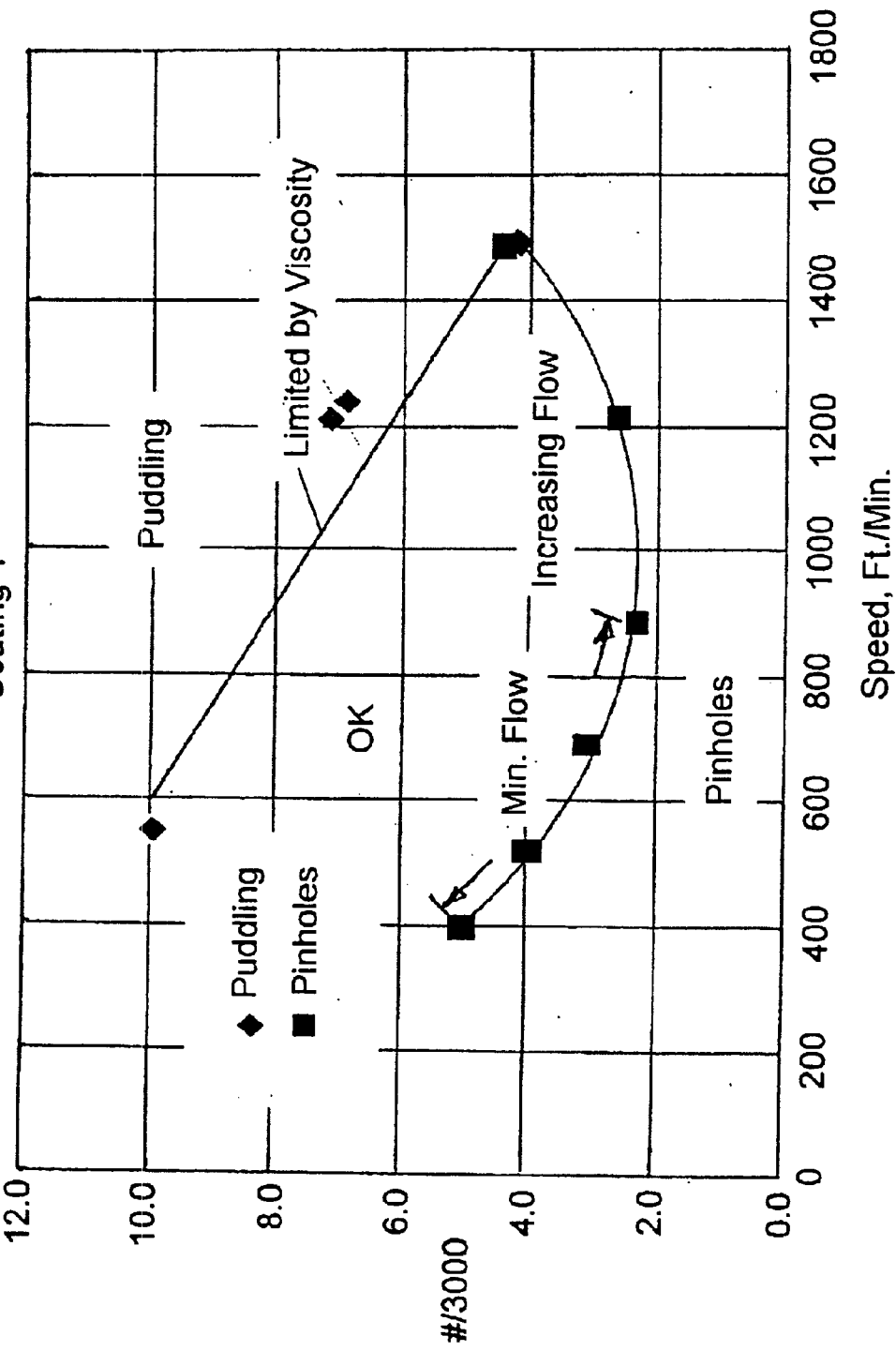
FIG. 5 is a plot of coat weight versus speed.

For any given target coat weight and speed, there are a range of viscosities, stretch, and acceleration numbers that will allow the coating to run well. As shown in FIG. 5, the minimum flow rate found to date for screening coating properties is 0.015 gallons/inch/minute or 0.38 cc/cm/sec. This represents a coat weight and speed of 2.4 lb/3000 sq. ft. at 1,000 ft./min. Using this test to identify new materials, it is expected that the minimum flow rates will be even lower. The stretch measurement may be converted into dynes/cm based on a known density of the coating material, the known value for acceleration due to gravity, and a known fixed distance that the coating travels to reach the 10 cc graduated cylinder 19. The standard deviation among at least four trials per sample should be ±1.0 dyne/cm.

The lower coat weight boundary of FIG. 5 is described by the momentum of the falling curtain and the momentum of the impinging air stream caused by the velocity of the web. For the left-hand portion of the pinhole-limited coat weight curve, the landing momentum of the curtain exceeds the momentum of the impinging air. The coat weight and speed curve is determined by the minimum flow rate out of the die. At some speed, 900 feet/minute as shown in FIG. 5, the momentum of the air equals the momentum of the curtain. Above this speed, the curtain needs more momentum to prevent the air from penetrating under the curtain to cause pinholes. The only way to get more momentum is to increase the flow rate and so the coat weight at the right-hand portion of the curve rises.

The puddling limit, or the upper limit of the coat weight speed operating window is caused by insufficient lateral force imparted by the web to make all of the coating leave with the sheet. Once again, force equals momentum. The lateral force imparted by the sheet gets into the body of the coating through the coating viscosity. Higher viscosities will generate a larger force, and thus allow a heavier coat weight to be run. As speed is increased, more momentum is needed, but the acceleration through viscosity is limited, so that the coat weight must drop. At a certain speed, the puddling limit and pinhole limit converge. As shown in FIG. 5, the convergence limit is 1550 feet/minute.

Measuring the momentum of a falling round stream by determining its flow rate and velocity indicate the same performance as for a curtain.

In step 40a of FIG. 2, velocity can optionally be measured by deflecting the stream of coating 17 sideways using an air stream of known force from an air nozzle and measuring the angle of deflection.

Figure 3:
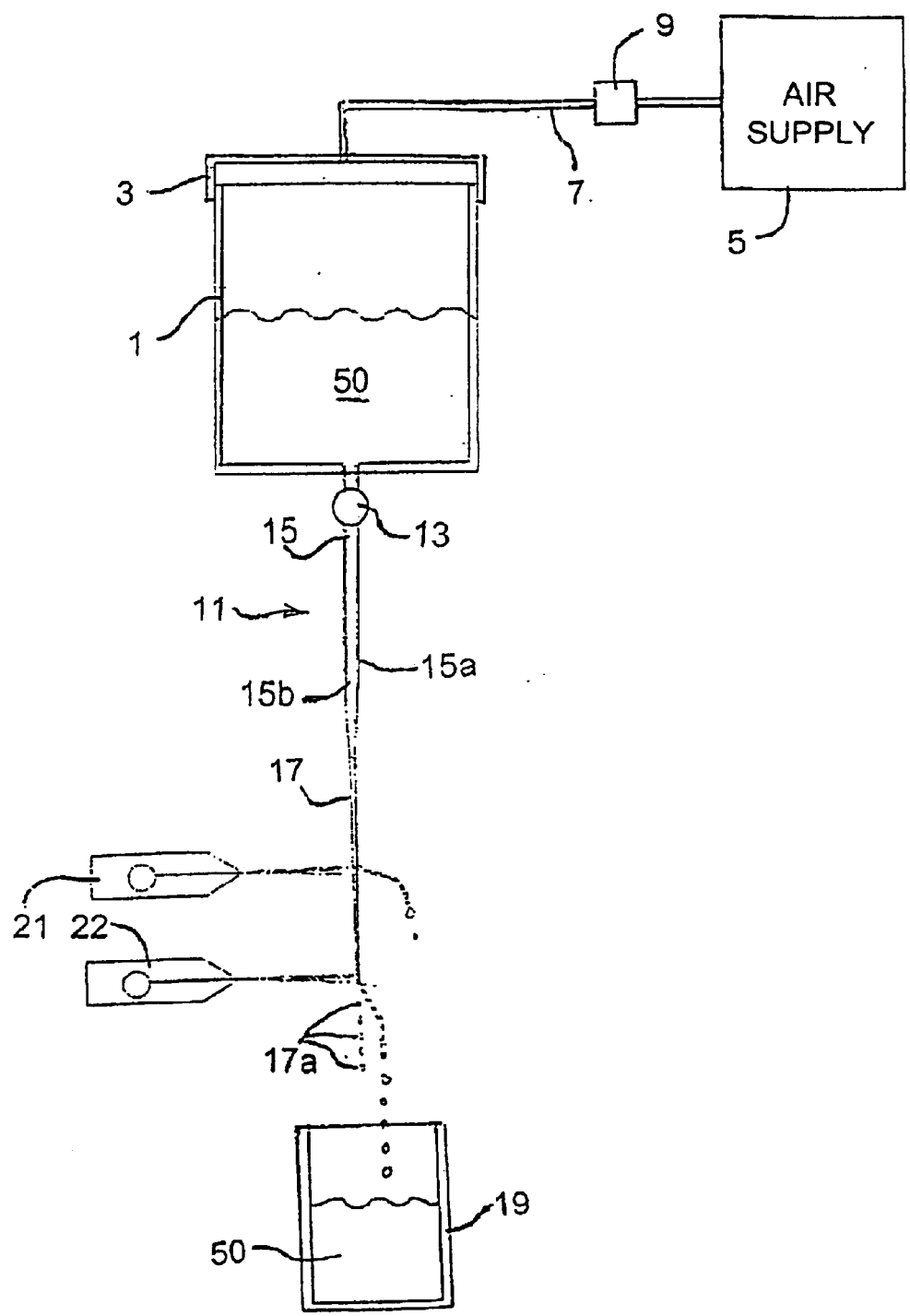
FIG. 3 is a view similar to FIG. 1 showing additional aspects of the invention.

In order to measure acceleration, two velocities are needed. As illustrated in FIG. 3, two air nozzles 21 and 22 are placed near the stream at two different heights from the outlet 15b of the tube 15. The distance of the stream from the nozzles 21, 22 is constant.

Figure 4:
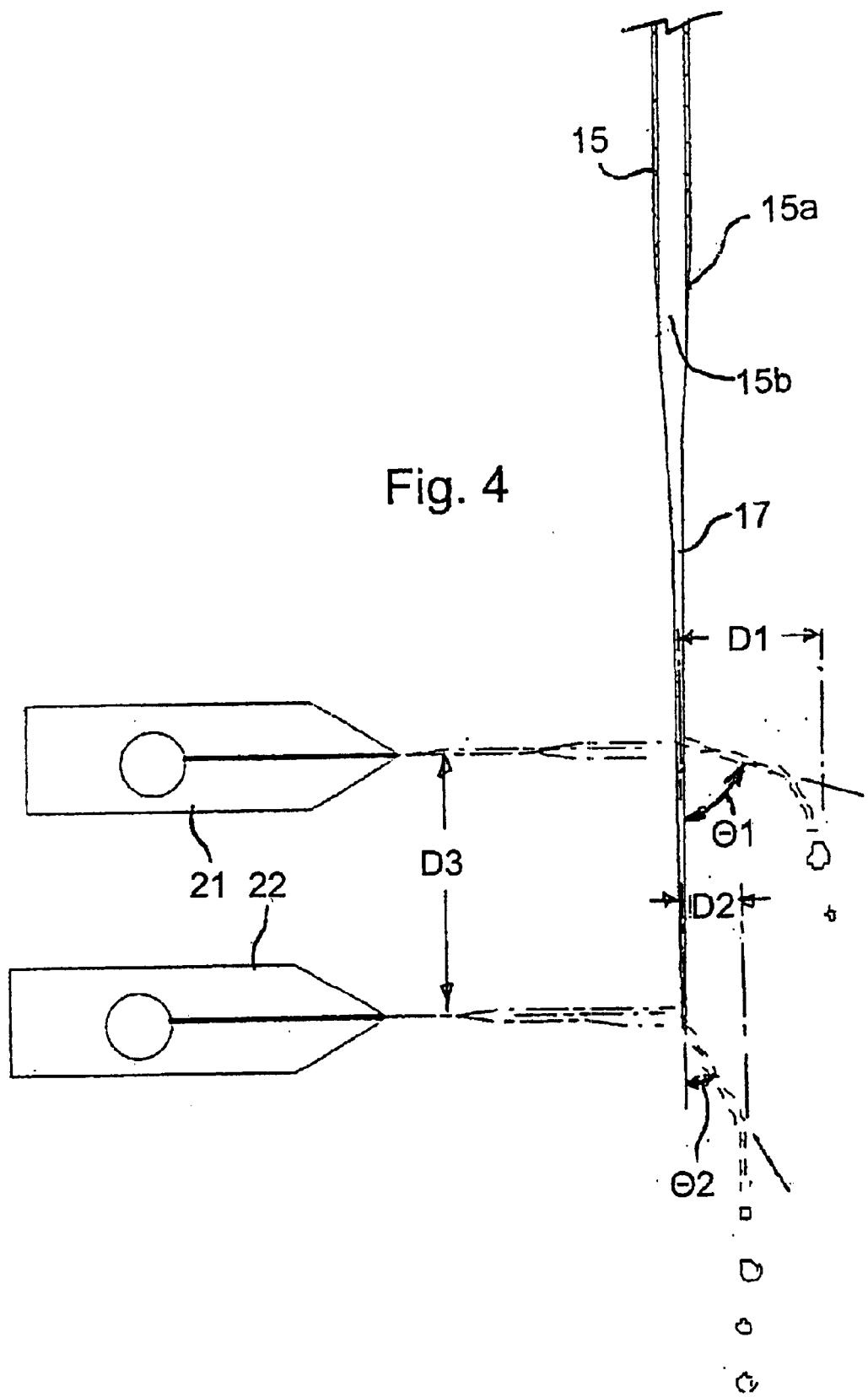
FIG. 4 is an enlarged detail of FIG. 3.

FIG. 4 illustrates how the deflection $D_1$ at angle $\Theta_1$ at the upper nozzle 21 is more than the deflection $D_2$ at $\Theta_2$ at the lower nozzle 22.

A smaller deflection means the falling stream has more momentum. The force of the falling stream is given by:

Fs=Fa tan $\Theta$ where Fa is the known force of the air stream and $\Theta$ is the measured angle of deflection.

Since force (Fs) equals momentum for the stream, the momentum is known.

Fs=QV where Q is the flow rate and V the velocity. Measuring the flow rate, gives the local falling velocity. The flow rate is set to the minimum that will form a continuous stream at the lower nozzle position.

Accordingly, both the upper and lower velocities can be calculated from the horizontal force of the air from the nozzles 21, 22, and the angle of deflection given the vertical force of the falling stream of coating. Velocities at two different heights yield the acceleration. The time of the fall is the distance (the known distance $D_3$ between the nozzles 21, 22) divided by the average velocity. The effective acceleration is the difference in velocities divided by the time of the fall.

The pressure of the air flow can be calculated from the air flow of the nozzle 21. The pressure, relative to the air flow, is adjusted to keep the angles of deflection in a sensitive range for the flow rate being tested, but the final acceleration calculation is not dependent on the pressure. Representative values are in the following table:

| Orifice Flow time | Inches sec/10 ml | 33.18 | 33.18 | 64.05 | 62 |
|---|---|---|---|---|---|
| Angle, upper | deg | 63 | 63 | 70 | 70 |
| Angle, lower | deg | 32 | 32 | 32 | 32 |
| Density | #/gal | 8.28 | 8.28 | 8.28 | 8.28 |
| Air flow | L/min | 4.2 | 4.2 | 4.2 | 4.2 |
| Distance of fall | inches | 1.25 | 1.25 | 1.25 | 1.25 |
| Distance to upper nozzle | inches | 0.15 | 0.15 | 0.15 | 0.15 |
| Qs | ml/min | 18.08318264 | 18.08318 | 9.367681 | 9.677419 |
| | | Upper | | | |
| Pa (0.040" high) | Inches of water | 0.776896026 | 0.776896 | 0.776896 | 0.776896 |
| Pa | #/horizontal inch | 0.001189622 | 0.00119 | 0.00119 | 0.00119 |

-continued

| | | | | | |
|---|---|---|---|---|---|
| tan Θ | | 1.962610506 | 1.962611 | 2.747477 | 2.747477 |
| mass flow - m | #/sec | 0.000663847 | 0.000664 | 0.000344 | 0.000355 |
| Upper Velocity | ft/sec | 0.89689253 | 0.896893 | 0.892388 | 0.882759 |
| area | sq. cm | 0.011024737 | 0.011025 | 0.00574 | 0.005994 |
| Lower Velocity | | | | | |
| tan Θ | | 0.624869352 | 0.624869 | 0.624869 | 0.624869 |
| Lower Velocity | ft/sec | 1.924284812 | 1.924285 | 2.396245 | 2.370389 |
| Lower area | sq. cm | 0.005138535 | 0.005139 | 0.002138 | 0.002232 |
| Gravity accel | ft/sec | 3.259972145 | 3.259972 | 2.919573 | 2.932056 |
| Time of fall | sec | 0.07385 | 0.07385 | 0.06335 | 0.06404 |
| Effective acceleration | ft/sec/sec | 13.91 | 13.91 | 23.74 | 23.23 |
| Momentum | lbs. | 3.8686E−05 | 3.87E−05 | 2.5E−05 | 2.55E−05 |

Figure 6A:
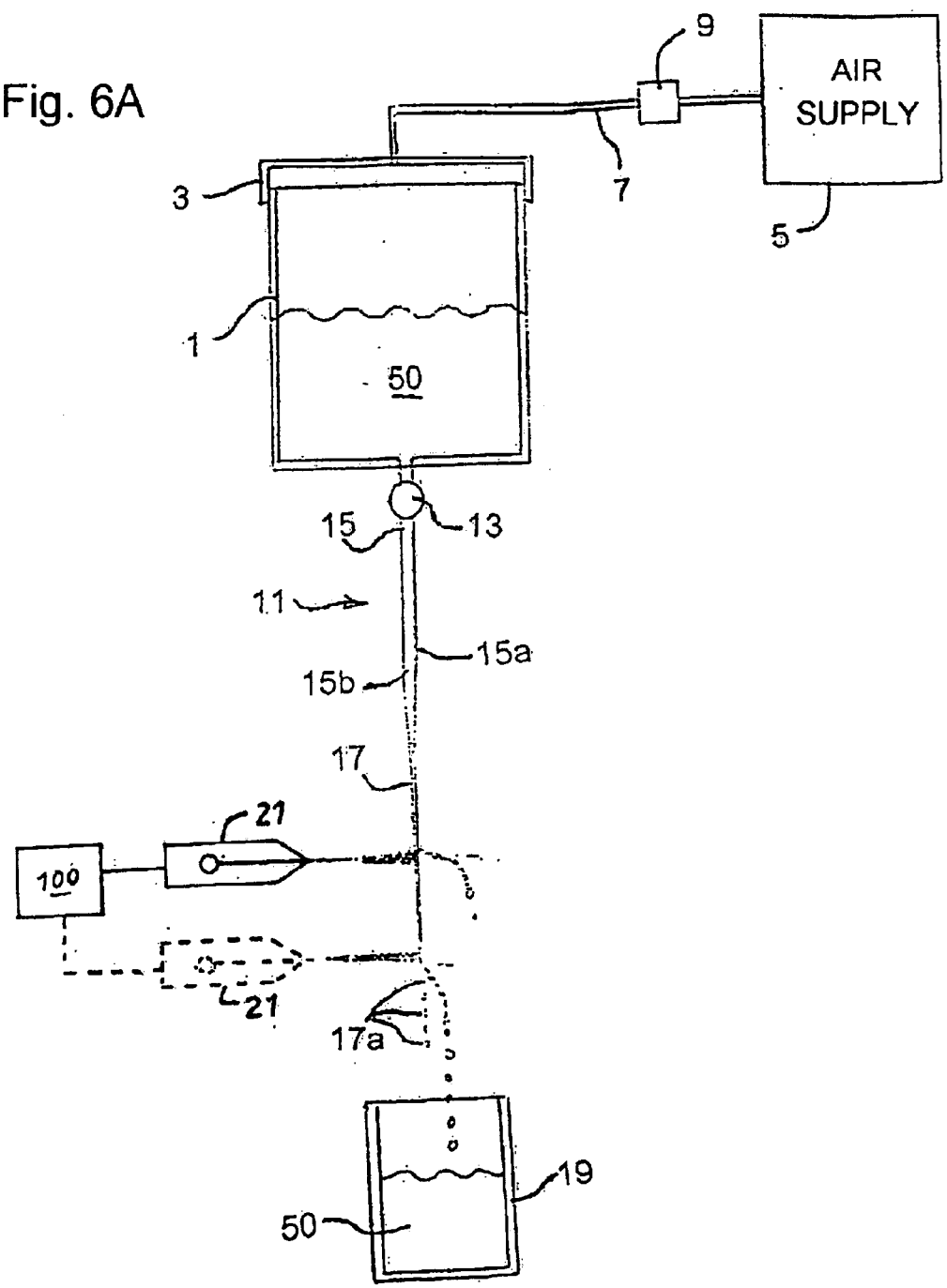
FIGS. 6A & 6B are schematic diagrams of alternative measurement setups used with the apparatus of FIG. 1.
Figure 6B:
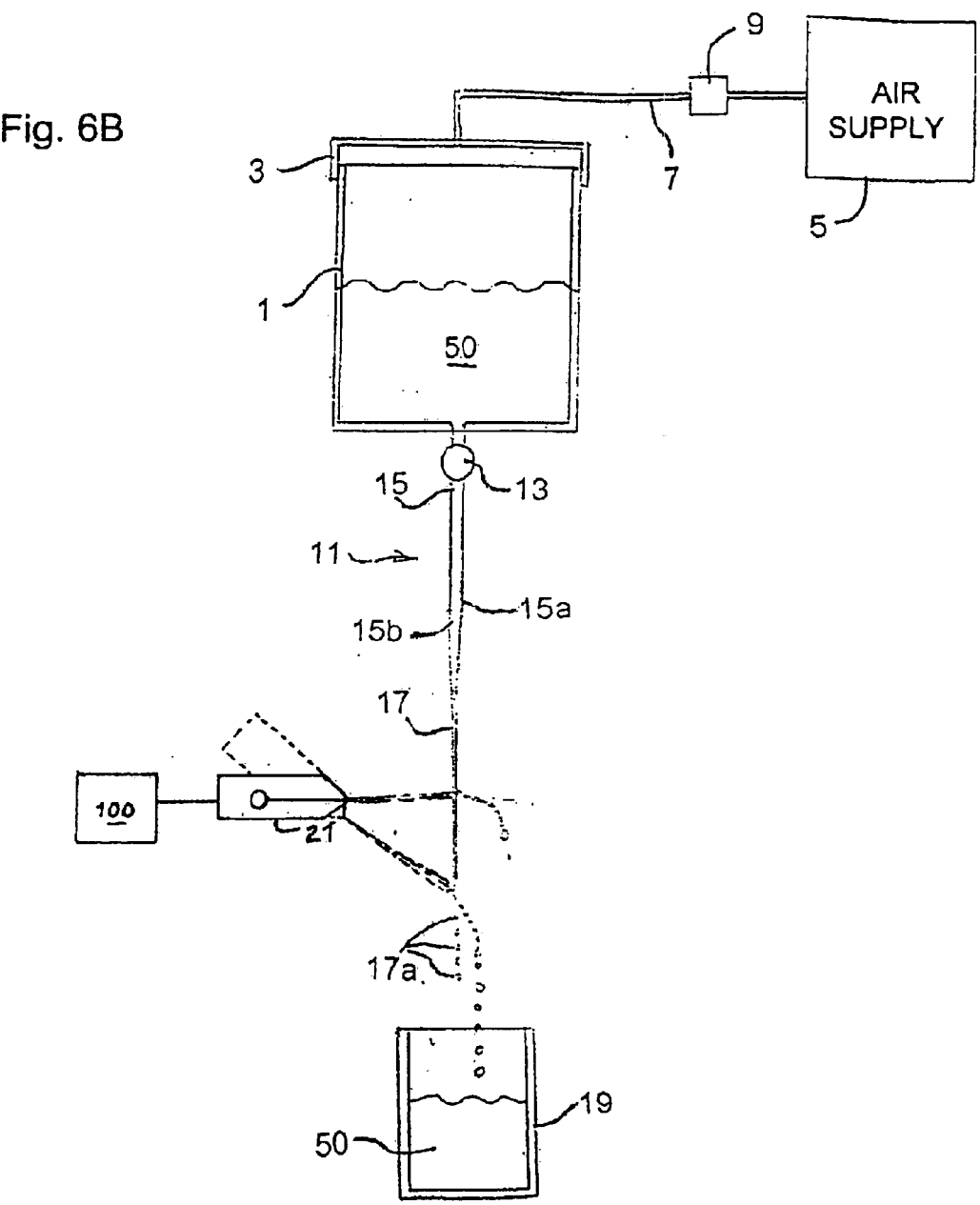

FIGS. 6A & 6B illustrate two different embodiments of the apparatus of FIG. 1 having only one air nozzle 21 for measuring acceleration of the stream of coating 17. The nozzle 21 is arranged to either move vertically, as in FIG. 6A, or to pivot on an axis as shown by FIG. 6B. A motivator 100 is provided in working relationship with nozzle 21 for either moving the nozzle 21 vertically or pivoting the nozzle 21 between two positions.

In FIG. 6A, the motivator 100 positions the nozzle 21 between two known, fixed heights along the path of the stream of coating 17. The motivator may be a threaded rod on which the nozzle 21 is mounted, a chain drive, or other mechanical drive for moving the nozzle accurately, and preferably quickly as well. The nozzle 21 repositioned at the second height is illustrated in dashed lines. The heights may be the same as those used when two nozzles 21, 22 are provided. The distance of the nozzle 21 to the coating 17 is kept constant as well, so that the deflection measurements at each of the two different heights may be used as described above in the case illustrated by FIG. 3 where two nozzles are used.

Similarly, in FIG. 6B, the motivator 100 is used to pivot the air nozzle 21 between two different angle orientations relative to the stream of coating 17, so that the air flow from the nozzle 21 can be directed at two different heights on the stream of coating 17. Preferably, one orientation is horizontal, and the second orientation is at an oblique angle to the coating 17. The nozzle 21 is used to generate different deflections in the stream of coating 17 from each of the two orientation angles. That is, the air flow from the nozzle 21 is directed at each of the two different known heights along the stream of coating 17 to deflect the stream a measurable amount.

Based on the known information, including the angles at which the nozzle 21 is oriented to direct an air stream, the force of the air stream and the distance of the nozzle to the stream of coating 17 at each angle of orientation, the acceleration of the stream of coating 17 can be calculated as above, with appropriate adjustment for the angled orientation of the nozzle 21 in at least the second position.

In a further alternative to the technique of FIGS. 6A & 6B, a single deflection measurement can be taken using a single air nozzle 21, without moving the air nozzle. The velocity of the stream can be used alone to evaluate the coating stream 17. Or, the acceleration at the measured point can be calculated using known mathematical relationships between acceleration and velocity, provided the air nozzle 21 is located at a known distance along the falling stream of coating 17. The method and apparatus of the invention are increasingly accurate with more measurement points, but a single point may be sufficient to evaluate the stream of coating 17 in some situations.

Although the equipment used is the apparatus according to FIGS. 1 or 3 with the flow rate measured using a 10 cc-graduated cylinder 19 and a stopwatch, the process could be automated electronically. One could measure the flow rate with a known hot wire anemometer for example. This would provide the same information with more precision in less time. Alternatively, the two air nozzles 21, 22 could be cycled on and off with the stream deflections measured optically. An automated version can also be used with an online indicator.

The landing velocity of a coating as it makes contact with a substrate or web is also a critical parameter for determining whether a coating will run properly. The landing velocity can be determined from a combination of the stretch and acceleration measurements with a viscosity measurement of the coating. Viscosity measurement is known in the art by various methods such as capillary, cone and plate, and concentric cylinder viscometers.

Measuring all of the essential dynamic fluid properties effectively predicts the necessary performance for producing a coating that can be applied with a curtain coater.

While specific embodiments of the invention has been shown and described in detail to illustrate the application of the principles of the invention, it will be understood that the invention may be embodied otherwise without departing from such principles.

What is claimed is:

1. An apparatus for testing a coating fluid for runnablilty, the fluid having surface tension, viscosity, elasticity and dilatant behavior which influence the stretch of the fluid, the apparatus comprising:

a pressurized container adapted for receiving a quantity of the coating fluid, the container having an outlet arrangement;

the outlet arrangement comprising a tube and flow rate regulating means for regulating a flow rate of the fluid through the tube, the tube having an opening for discharging the fluid which falls under the influence of gravity, the flow rate regulating means being operated to adjust the flow rate of the fluid until a continuous, ripple-free stream of fluid leaves the opening; and flow rate measuring means for measuring a minimal flow rate at which the fluid leaves the opening in the continuous, ripple-free stream, the runnability and stretch being a function of the measured minimum flow rate.

2. An apparatus according to claim 1, wherein the opening of the tube has a diameter of about 0.011" to about 0.034".

3. An apparatus according to claim 2, wherein the opening of the tube has a diameter of about 0.015" to about 0.030".

4. An apparatus according to claim 1, including means for supplying air to the container to pressurize the container.

5. An apparatus according to claim 4, wherein the means for supplying air comprising a storage tank of air connected to the container via an air tube and an air-pressure valve.

6. An apparatus according to claim 1, wherein the flow rate measuring means comprises a graduated volume below the tube opening for receiving the fluid leaving the opening and a time measuring device for measuring the time it take for the fluid to fill a selected part of the volume.

7. An apparatus according to claim 1, wherein the flow rate regulating means comprises a needle valve in the tube.

8. An apparatus according to claim 1, wherein the flow rate measuring means comprises a flow meter.

9. An apparatus according to claim 1, wherein the tube has a tapered end with a knife-edge forming said opening for discharging the fluid which falls under the influence of gravity.

10. An apparatus for testing a coating fluid, the fluid having surface tension, viscosity, elasticity, and dilatant behavior which influence the failing acceleration of the fluid under the influence of gravity, the apparatus comprising:
   a pressurized container adapted to receive the fluid, the container having an outlet opening;
   means for regulating a flow rate of the fluid through the outlet opening for creating a continuous stream of fluid falling from the outlet opening under the influence of gravity;
   air nozzle means for blowing a stream of gas at the continuous stream at each of two different heights for deflecting the continuous stream at each of the two different heights by an angle that is proportional to a velocity times flow rate or momentum of the continuous stream, at each respective height, the air nozzle means comprising two air nozzles spaced vertically from each other and each nozzle spaced a known horizontal distance from the continuous stream; and
   means for calculating the acceleration of the continuous stream as a function of the velocity of the continuous stream at the two different heights and the distance between the two different heights.

11. A method for measuring coating fluid runnability which is related to stretch and combined effects of surface tension, viscosity, elasticity and dilatant behavior of the fluid, the method comprising the steps of:
   loading a container with a quantity of fluid;
   pressurizing the container;
   releasing the fluid from an outlet tube opening of the container to fall from the opening at a flow rate;
   regulating the flow rate so that the fluid forms into a continuous stream from the opening; and
   measuring a minimal flow rate at which the fluid leaves the opening in the continuous stream, the runnability and stretch being a function of the measured minimum flow rate.

12. A method according to claim 11, including pressurizing the container with air.

13. A method according to claim 12, wherein the minimal flow rate is established by increasing an initial flow rate of a series of drops with coarse and fine adjustment until the fluid transforms into the continuous stream.

14. A method for measuring the acceleration of a fluid, comprising:
   loading a container with a fluid;
   pressurizing the container;
   releasing a continuous stream of the fluid from an outlet of the container at a flow rate to form a continuous stream of the fluid;
   horizontally deflecting the continuous stream of the fluid by blowing first and second air flows at the continuous stream, the first and second air flows being directed at two different heights along the continuous stream and deflecting the continuous stream at each height by a deflection angle proportional to the velocity times the flow rate or the momentum of the continuous stream at each height; and
   calculating the acceleration of the stream as a function of the velocity of the stream at the two different heights and the spacing between the two different heights;
   the first and second air flows being provided by nozzle means for directing air at a known horizontal force at each of the two different heights, the nozzle means comprising two vertically spaced apart air nozzles positioned at known horizontal distances from the continuous stream.

15. An apparatus for testing a coating fluid, the fluid having surface tension, viscosity, elasticity and dilatant behavior which influence the failing acceleration of the fluid under the influence of gravity, the apparatus comprising:
   a pressurized container adapted to receive the fluid, the container having an outlet;
   the outlet comprising a tube with an opening and means for regulating a flow rate of the fluid through the tube and out the opening for creating a continuous stream of fluid falling from the opening under the influence of gravity;
   air nozzle means for blowing a stream of gas at the continuous stream at a known distance from the outlet, the stream of gas for deflecting the continuous stream at an angle that is proportional to a velocity times flow rate or momentum of the continuous stream; and
   means for calculating the acceleration of the continuous stream as a function of the velocity of the continuous stream.

16. An apparatus according to claim 15, wherein the air nozzle means comprises a single air nozzle.

17. An apparatus according to claim 15, including means for supplying air to the container which comprises a storage tank of air connected to the container via an air tube and an air-pressure valve.

18. An apparatus according to claim 15, including a volume measuring device and a time recording device for measuring the flow rate of the fluid from the tube opening.

19. A method for measuring the acceleration of a fluid, comprising:
   loading a container with a fluid;
   pressurizing the container;
   releasing a continuous stream of fluid from an outlet of the container at a flow rate to form a continuous stream of fluid;
   horizontally deflecting the continuous stream of fluid by blowing an air flow at the continuous stream at a known height and deflecting the continuous stream by a deflection angle proportional to the velocity times flow rate or momentum of the continuous stream at the known height; and
   calculating the acceleration of the stream as a function of the velocity of the stream.

20. A method according to claim 19, including pressurizing the container with air.

21. A method according to claim 19, wherein the flow rate is established by increasing an initial flow rate of a series of drops of the fluid from the outlet until the fluid transforms into a continuous falling stream.

* * * * *